USO05573551A

United States Patent [19]
Lin et al.

[11] Patent Number: 5,573,551
[45] Date of Patent: Nov. 12, 1996

[54] IMPLANTABLE MEDICAL DEVICE WITH DETACHABLE BATTERY OR ELECTRONIC CIRCUIT

[75] Inventors: Jack H. Lin, Lake Jackson; Richard A. Walkuski, Sr., Angleton, both of Tex.

[73] Assignee: Intermedics, Inc., Angleton, Tex.

[21] Appl. No.: 360,586

[22] Filed: Dec. 21, 1994

Related U.S. Application Data

[63] Continuation-in-part of Ser. No. 146,904, Nov. 1, 1993, Pat. No. 5,411,538.

[51] Int. Cl.$^6$ ................................................ A61N 1/375
[52] U.S. Cl. .................................................... 607/33; 607/2
[58] Field of Search ........................... 607/2, 33, 34, 607/36, 37, 116, 119

[56] References Cited

U.S. PATENT DOCUMENTS

| | | |
|---|---|---|
| 4,010,760 | 3/1977 | Kraska et al. ............................ 607/36 |
| 4,119,103 | 10/1978 | Jirak ......................................... 607/9 |
| 4,787,389 | 11/1988 | Tarjan ....................................... 607/4 |
| 4,933,988 | 6/1990 | Thibault ................................... 455/349 |
| 5,161,527 | 11/1992 | Napphulz et al. ....................... 607/4 X |
| 5,314,451 | 5/1994 | Mulier ..................................... 607/33 |

FOREIGN PATENT DOCUMENTS

| | | | |
|---|---|---|---|
| 2466256 | 4/1981 | France ...................................... 607/36 |
| 0146388 | 2/1981 | Germany .................................. 607/33 |
| 0229033 | 10/1985 | Germany .................................. 607/36 |
| 1274882 | 5/1972 | United Kingdom ..................... 607/33 |

*Primary Examiner*—William E. Kamm
*Assistant Examiner*—Jeffrey R. Jastrzab
*Attorney, Agent, or Firm*—John R. Merkling

[57] ABSTRACT

An implantable medical device, such as a pacemaker, cardioverter or defibrillator, having a detachable power source, so that either the power source or the electronic circuitry can be replaced. The electronic circuitry is enclosed within a first container and the battery or power source is enclosed within a second container. The two containers are coupled by tracks slidingly connecting the containers along substantially planar sections thereof. In a first embodiment, the tracks comprise dovetail tongue and groove configurations. In a second embodiment, the tracks comprise a bayonet-type connection having male and female parts. The male part comprises two parallel arms. The female part comprises two parallel rails having a relatively inflexible section adjacent a distal end of the rail. Proximally on the rail, there is a relatively flexible section. A tab at the flexible section can be pressed inwardly against the arm to release the arms and allow them to be withdrawn from the female part, without the use of an additional tool. In a third embodiment, the containers are connected by sheaths and blades. The sheaths completely enclose the blades. The blades have two parallel arms connected at proximal ends of the arms by a cross piece. The arms are slightly flexible or bendable. On each arm there is a tab which engages a notch in the side wall of the sheath when the blade is inserted into the sheath.

14 Claims, 5 Drawing Sheets

IMPLANTABLE MEDICAL DEVICE WITH DETACHABLE BATTERY OR ELECTRONIC CIRCUIT

This is a Continuation-in-part of application Ser. No. 08/146,904 filed on Nov. 1, 1993 now U.S. Pat. 5,411,538.

FIELD OF OUR INVENTION

Our invention is directed towards an implantable medical device such as a cardiac pacemaker or a cardioverter-defibrillator, and more specifically towards a cardiac stimulator having a replaceable battery or a replaceable electronic circuit.

BACKGROUND OF OUR INVENTION

Electrically driven implantable devices are used principally as cardiac pacemakers, but they have also been considered for defibrillators; for heart assist, or drug infusion and dispensing systems; for bone growth and repair, pain suppression, or scoliosis treatment; for artificial vision, heart, or larynx; for stimulation of brain, nerves, muscle, gut or bladder; and for implanted sensors. For purposes of this disclosure, an implantable cardiac pacemaker/defibrillator is given as an example.

The basic pacemaker system consists of an electrode attached to the heart and connected by a flexible lead to a pulse generator. This generator is a combination of a power source and the microelectronics required for the pacemaker system to perform its intended function. A fixed rate pacemaker provides continuous pulses to the heart, irrespective of proper heart beating, while a demand inhibited pacemaker provides pulses only when the heart fails to deliver a natural pulse. Depending upon various sensed events, the pacemaker stimulates the right atrium, the right ventricle, or both chambers of the heart in succession. The pacemakers in current use incorporate circuits and antennae to communicate non-invasively with external instruments called programmers. Most of today's pacemakers are of the demand inhibited type, hermetically sealed, and programmable.

The longevity of pacemakers has been limited primarily by the capacity of their power sources. Early pacemakers were powered by primary zincmercuric oxide cells. Although this system was used for about 15 years, it did suffer from high self-discharge and hydrogen gas evolution. Because of gas evolution, the pacemaker could not be hermetically sealed, and had to be encapsulated in heavy epoxy. In 1970, the average life of the pulse generator was only 2 years, and 80 percent of explants were necessitated by failed batteries.

Consideration was given to many means of power generation and power storage. This included primary chemical batteries of all sorts, nuclear batteries, rechargeable batteries, and the separation of the stimulator system into two parts, with the power pack being outside the patient's body and transmitting pulses of energy to a passive implanted receiver and lead. Cardiac pacemakers based on rechargeable nickel-cadmium systems and rechargeable zinc-mercuric oxide systems were developed. Such pacemakers are described in prior art references, including U.S. Pat. Nos. 3,454,012; 3,824,129; 3,867,950; 3,888,260; and 4,014,346. The rechargeable pacemaker incorporated a charging circuit which was energized by electromagnetic induction, or other means. A replaceable battery has also been proposed by Kraska, et al, U.S. Pat. No. 4,010,760.

Because the power supply or battery has generally been the limiting component in both implantable pacemakers and implantable defibrillators, it would be advantageous to provide a implantable cardiac stimulator which has a replaceable battery. Thus, instead of replacing the entire stimulator, only the battery need to be replaced as the power source nears its ends of life. Alternatively, a faulty or obsolete electronic circuit could be replaced or a circuit having different features could be substituted for the prior circuit. This should provide substantial economic benefits for the patient.

SUMMARY OF OUR INVENTION

We have invented an implantable medical device, such as a pacemaker, cardioverter or defibrillator, having a detachable power source, so that either the power source or the electronic circuitry can be replaced.

The electronic circuitry is enclosed within a first container and the battery or power source is enclosed within a second container. Our invention is specifically directed to means for mechanically coupling the first and second containers. We have invented means for mechanically coupling the two containers comprising track means for slidingly connecting the containers along substantially planar sections thereof. In a first embodiment of our invention, the tracks comprise dovetail tongue and groove configurations which permit the two containers to be securely connected. In a second embodiment of our invention, the track means comprise a bayonet-type connection having male and female parts. The male part comprises two parallel arms connected at a proximal end to one of the containers. At a distal end of the arms, there are outwardly directed prawls which will engage indentations in the female part. The female part comprises two parallel rails attached to the other container. The rails have a relatively inflexible section adjacent a distal end of the rail. The distal end of each rail will lie adjacent the proximal end of its engaging arm when assembled. Proximally on the rail, and adapted to lie adjacent the distal end of the arm, there is a relatively flexible section, forming an indentation. A tab at the flexible section can be pressed inwardly against the arm to release the arms and allow them to be withdrawn from the female part, without the use of an additional tool.

In our preferred embodiment, the stimulator comprises an electronics package having a header for connection to leads coupled to the patient's heart and a header-like coupler. The stimulator further comprises a battery pack having a second header-like coupler. The couplers mate together mechanically and are joined electrically by a separate pin. The pin has a configuration similar to the connection used for implantable leads, and preferably similar to the VS-1 standard for pacemaker leads, widely adopted in the pacemaker industry. The pin presents such a coupling on both ends thereof so that one end can extend into the coupler of the electronics package and another end can extend into the coupler of the battery package. Alternatively, such a connector or pin, having a male configuration, could be provided on either the electronics coupler or the battery coupler with a corresponding female configuration on the other coupler.

We will now describe a preferred embodiment of our invention with reference to the accompanying drawings.

DETAILED DESCRIPTION OF OUR PREFERRED EMBODIMENT

Figure 1:
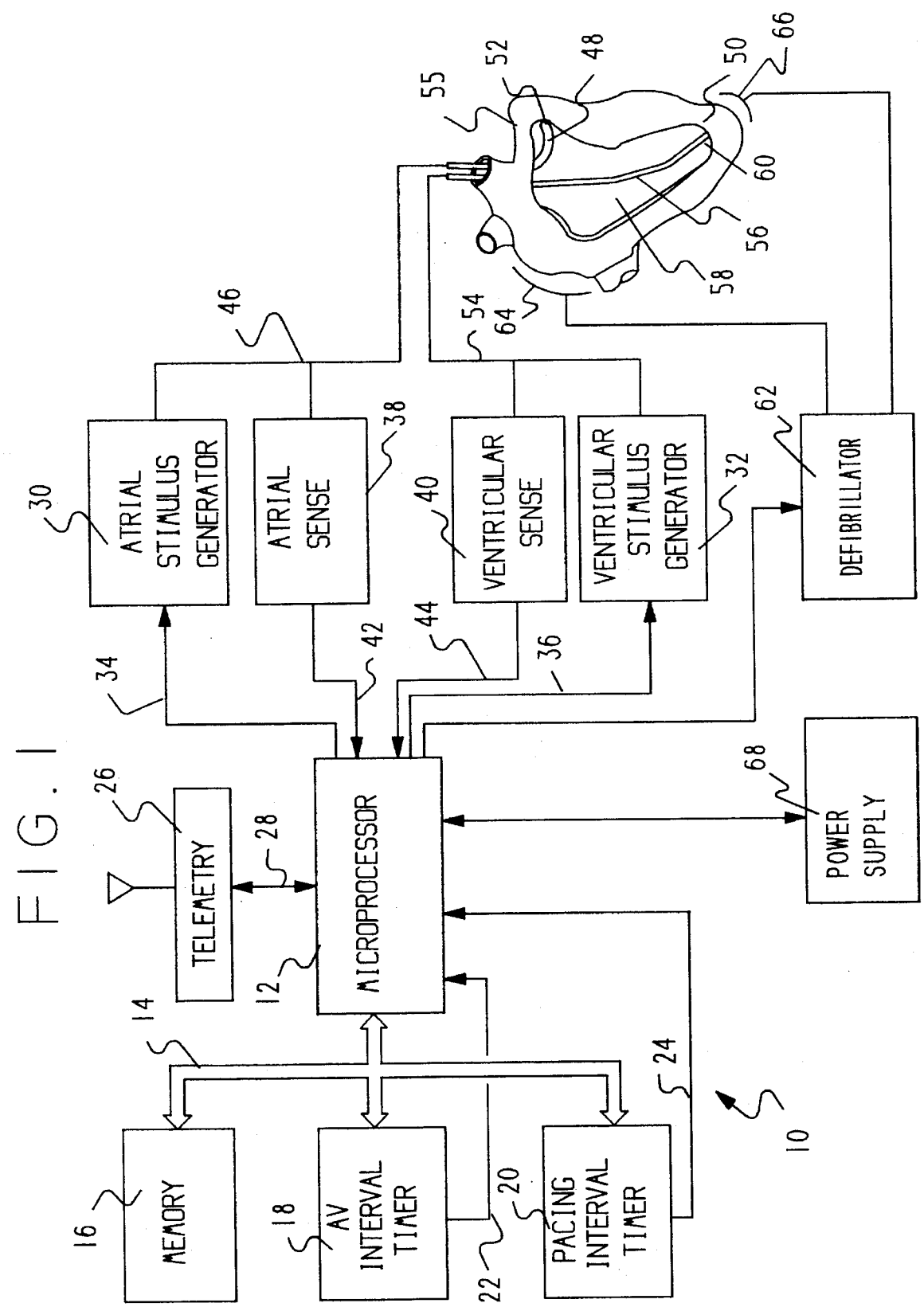
FIG. 1 is a block diagram of a pacemaker/defibrillator suitable for use in connection with our invention.

FIG. 1 is a block diagram illustrating an implantable pacemaker/defibrillator 10 according to our invention. A microprocessor 12 preferably provides pacemaker control and computational facilities. It will be appreciated that other forms of circuitry, such as analog or discrete digital circuitry can be used in place of microprocessor 12. However, a microprocessor is preferred for its miniature size and its flexibility, both of which are of critical importance in the implantable systems in which our invention will be used. A particularly energy efficient microprocessor which is designed specifically for such use is fully described in Gordon, et al., U.S. Pat. No. 4,404,972, which is also assigned to our assignee and the disclosure thereof is incorporated herein by reference.

The microprocessor 12 has input/output ports connected in a conventional manner via bi-directional bus 14 to memory 16, an A-V interval timer 18, and a pacing interval timer 20. In addition, the A-V interval timer 18 and pacing interval timer 20 each has an output connected individually to a corresponding input port of the microprocessor 12 by lines 22 and 24 respectively.

Memory 16 preferably includes both ROM and RAM. The microprocessor 12 may also contain additional ROM and RAM as described in the Gordon, et al. U.S. Pat. No. 4,404,972. The pacemaker operating routine is stored in ROM. The RAM stores various programmable parameters and variables.

The A-V and pacing interval timers 18 and 20 may be external to the microprocessor 50, as illustrated, or internal thereto, as described in the Gordon, et al. U.S. Pat. No. 4,404,972. The timers 18, 20 are suitable conventional up or down counters of the type that are initially loaded with a count value and count up to or down from the value and output a roll-over bit upon completing the programmed count. The initial count value is loaded into the timers 18, 20 on bus 14 and the respective roll-over bits are output to the microprocessor 12 on lines 22, 24.

The microprocessor 12 preferably also has an input/output port connected to a telemetry interface 26 by line 28. The implanted pacemaker is thus able to receive pacing and rate control parameters from an external programmer and send data to an external receiver if desired. Many suitable telemetry systems are known to those skilled in the art. One such system and encoding arrangement is described in Calfee, et al. U.S. Pat. No. 4,539,992 which is also assigned to our assignee. That description is incorporated herein by reference.

The microprocessor 12 output ports are connected to inputs of an atrial stimulus pulse generator 30 and a ventricle stimulus pulse generator 32 by control lines 34 and 36 respectively. The microprocessor 12 transmits pulse parameter data, such as amplitude and width, as well as enable/disable and pulse initiation codes to the generators 30, 32 on the respective control lines.

The microprocessor 12 also has input ports connected to outputs of an atrial sense amplifier 38 and a ventricular sense amplifier 40 by lines 42 and 44 respectively. The atrial and ventricular sense amplifiers 38, 40 detect occurrences of P-waves and R-waves respectively. The atrial sense amplifier 30 outputs a signal on line 42 to the microprocessor 12 when it detects a P-wave. This signal is latched to the microprocessor 12 input port by a conventional latch (not shown). The ventricular sense amplifier 40 outputs a signal on line 44 to the microprocessor 12 when it detects an R-wave. This signal is also latched to the microprocessor 12 input port by a conventional latch (not shown).

The input of the atrial sense amplifier 38 and the output of the atrial stimulus pulse generator 30 are connected to a first conductor 46, which passes through a conventional first lead 48. Lead 48 is inserted into a patient's heart 50 intravenously or in any other suitable manner. The lead 48 has an electrically conductive pacing/sensing tip 52 at its distal end which is electrically connected to the conductor 46. The pacing/sensing tip 52 is preferably lodged in the right atrium 54.

The input of the ventricular sense amplifier 40 and the output of the ventricular stimulus pulse generator 32 are connected to a second conductor 54. The second conductor 54 passes through a conventional second lead 56 which is inserted intravenously or otherwise in the right ventricle 58 of the heart 50. The second lead 56 has an electrically conductive pacing/sensing tip 60 at its distal end. The pacing/sensing tip 60 is electrically connected to the conductor 54. The pacing/sensing tip 60 is preferably lodged on the wall of the right ventricle 58.

The conductors 46, 54 conduct the stimulus pulses generated by the atrial and ventricular stimulus pulse generators 30, 32 respectively, to the pacing/sensing tips 52, 60. The pacing/sensing tips 52, 60 and corresponding conductors 46, 54 also conduct cardiac electrical signals sensed in the right atrium and right ventricle to the atrial and ventricular amplifiers, 38, 40 respectively. The sense amplifiers 38, 40 enhance the electrical signals. In the preferred embodiment of our invention, the amplifiers 38, 40, have an automatic gain control feature, as described in U.S. Pat: No. 4,903,699 to Baker, et al. That application is assigned to the same assignee as our present invention, and the disclosure thereof is incorporated herein by reference.

The implantable cardiac stimulator 10 may also have a defibrillator circuit 62. If fibrillation is detected through the atrial or ventricular sense amplifiers 38, 40 a high energy shock can be delivered through defibrillation electrodes 64, 66. Although patch-type electrodes 64, 66 are suggested, endocardial electrodes for defibrillation are also known.

Figure 2:
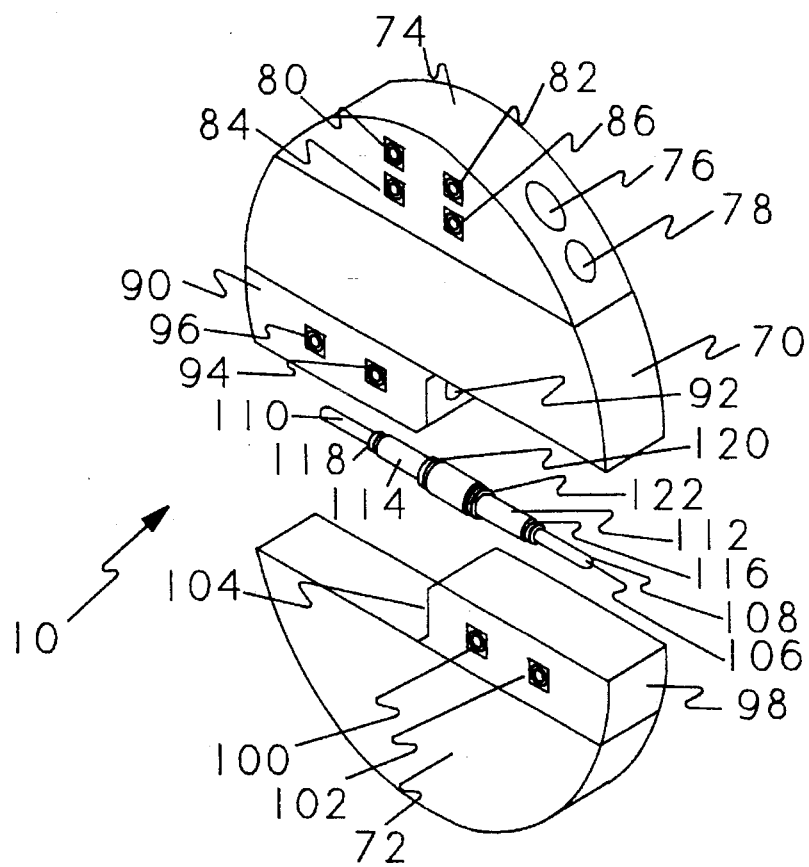
FIG. 2 is an exploded perspective view for the pacemaker/defibrillator according to our invention.
Figure 3:
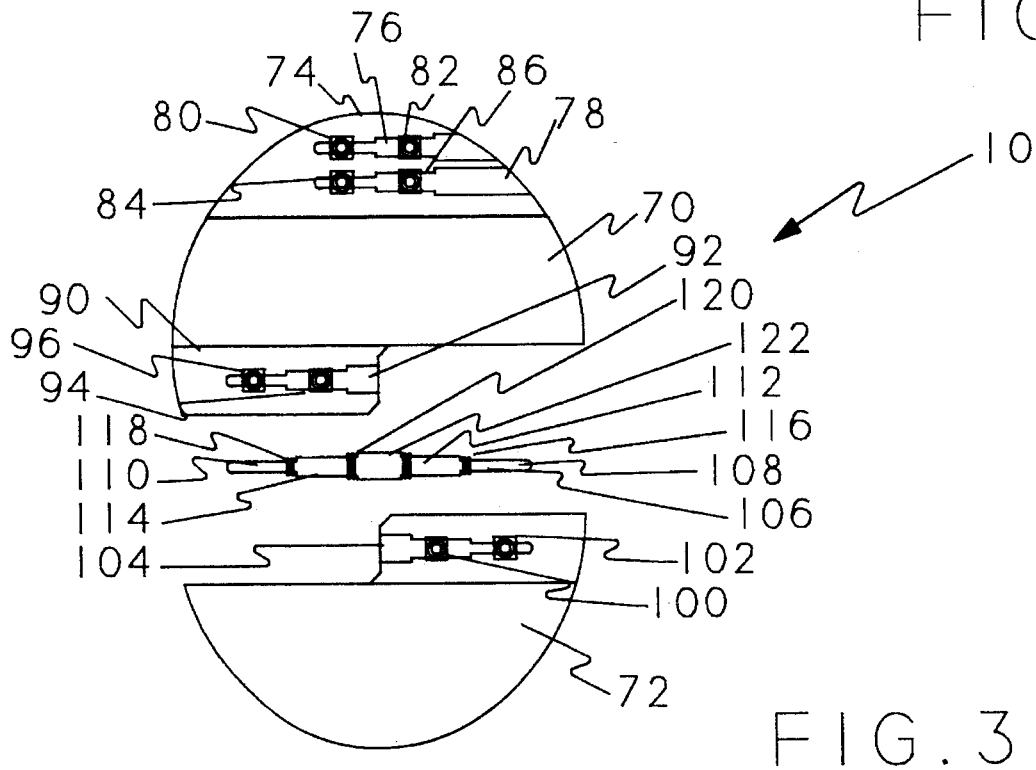
FIG. 3 is a front plan view of the pacemaker/defibrillator of FIG. 2.

The implantable cardiac stimulator 10 with detachable battery is shown in an exploded perspective view in FIG. 2 and in exploded plan view in FIG. 3. The stimulator 10 comprises an electronics container 70 which contains the microprocessor 12 and other electronic functions described above, with the exception of the power supply 68. The power supply 68 preferably comprises batteries contained in a battery container 72. The electronics container 70 has a header 74 provided with a plurality of female lead receptacles 76, 78. These receptacles preferably conform to the VS-1 voluntary industry standard for lead connections. Each of lead receptacles 76, 78 has associated with it connectors 80 and 82 and 84 and 86 respectively. The connectors 80, 82, 84, 86 secure leads in the receptacles 76, 78 with cap screws. Alternatively, the leads could be secured with a Sidelock (TM) connector such as that disclosed by Frey, et al., in U.S. Pat. No. 4,860,750. Whenever such cap-screw type connectors are mentioned herein, a Sidelock (TM) connector or other fastener could be substituted.

Opposite the header 74 on the electronics container 70 there is a first header-like coupler 90. The coupler 90 comprises a female receptacle 92 with two connectors 94, 96. The connectors 94, 96 may comprise cap screw type connectors as illustrated in FIGS. 2 and 3. Alternatively, the electronics container 70 and header-like coupler 90 may be comprised of a single metal enclosure, such as illustrated in FIGS. 4 through 7. The female receptacle 92 in these later instances is built into the coupler 90 on the container 70 and the connectors 94, 96 may comprise spring-type electrical connectors which extend into the interior of the female receptacle 92 to press against a pin which will be more particularly described below. The first coupler 90 mechanically interfaces with a second header-like coupler 98 on the battery container 72. The second coupler 98 also has two connectors 100 and 102 and a female receptacle 104. The connectors 100, 102 may comprise cap screw type connectors as illustrated in FIGS. 2 and 3. Alternatively, the battery container 72 and header-like coupler 98 may be comprised of a single metal enclosure, such as illustrated in FIGS. 4 through 7. The female receptacle 104 in these later instances is built into the coupler 98 on the container 72 and the connectors 100, 102 may comprise spring-type electrical connectors which extend into the interior of the female receptacle 104 to press against a pin which will be more particularly described below.

Both the receptacles 92 and 104 preferably conform with the VS-1 voluntary standard mentioned above. A special pin 106 is provided to couple both couplers 90, 98. This pin has conductors for the anode and cathode of both the battery and electronics couplers, each separated by integral o-rings. Thus, there is a battery cathode 108 and a corresponding electronics cathode 110 in electrical communication with the battery cathode 108. Similarly, there is a battery anode 112 and a corresponding electronics anode 114, in electrical communication with the battery anode 112. O-ring seals 116 are provided between the battery anode 112 and cathode 108. Similarly, o-ring seals 118 are provided between the electronics anode 114 and cathode 110. Finally, additional o-ring seals 120, 122, between the electronics anode 114 from the battery anode 112 (and also, therefore, between the two cathodes which are beyond the anodes) are used to prevent moisture from migrating into the receptacles 92 and 104 and inducing any leakage.

Figure 4:
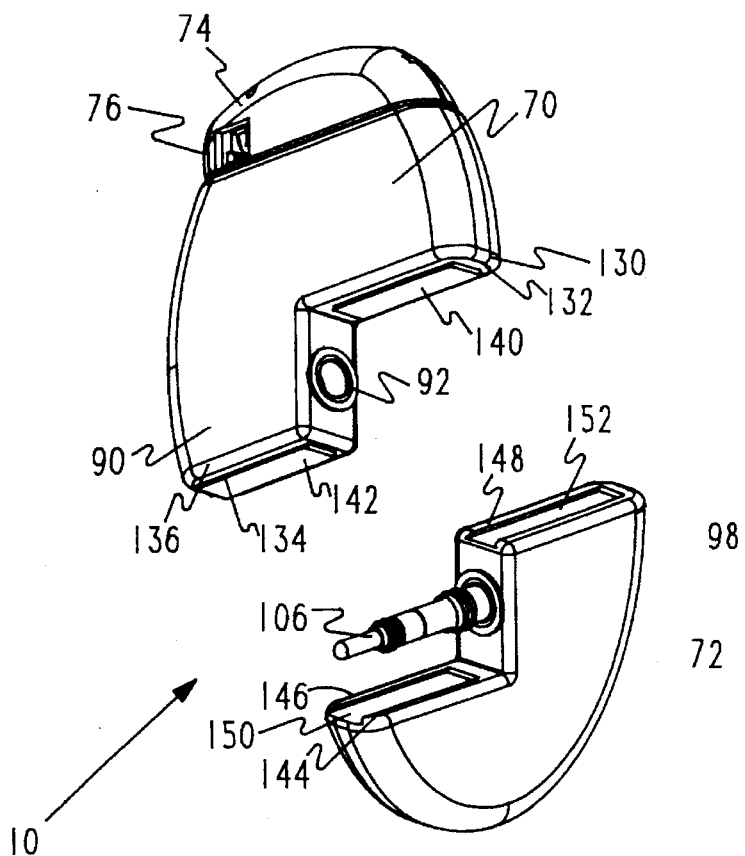
FIG. 4 is a perspective view of a disassembled pacemaker/defibrillator according to a first embodiment of our invention.

FIG. 4 illustrates in perspective view a first preferred embodiment of the implantable medical device of our invention having means for mechanically coupling the container 70 enclosing the electronic circuitry and the container 72 containing the battery. The container 70 comprises a bottom side 130 having a first substantially planar section 132. This substantially planar section 132 is parallel to a long axis of the pin 106, but offset therefrom. A second substantially planar surface 134 extends parallel to the first planar surface 132 on a distal end 136 of the first coupler 90. The first planar surface 132 and the second planar surface 134 are on opposite sides of the pin 106. A dovetail tongue 140 extends along the first planar surface 132 parallel to the axis of the pin 106. Similarly, a second dovetail tongue 142 extends along the second planar surface 134 parallel to the axis of the pin 106.

The container 72 for the battery comprises a top side 144. The top side 144 has a third substantially planar surface 146 extending parallel to the axis of the pin 106 and offset therefrom. The top side 144 further comprises a fourth planar surface 148 on the second coupler 98. The fourth planar surface 148 is parallel to the third planar surface 146, but offset therefrom. The third and fourth planar surfaces 146, 148 lie on opposite sides of the pin 106 and are adapted to mate with the second and first planar surfaces respectively.

A dovetail groove 150 extends along the third planar surface 146 parallel to the axis of the pin 106. A second dovetail groove 152 extends along the fourth planar surface 148, parallel both to the axis of the pin 106 and to the first groove 150. The dovetail tongues 140, 142 and grooves 150, 152 form track means for slidingly connecting the containers 70, 72 to one another in a secure mechanical attachment.

Figure 5:
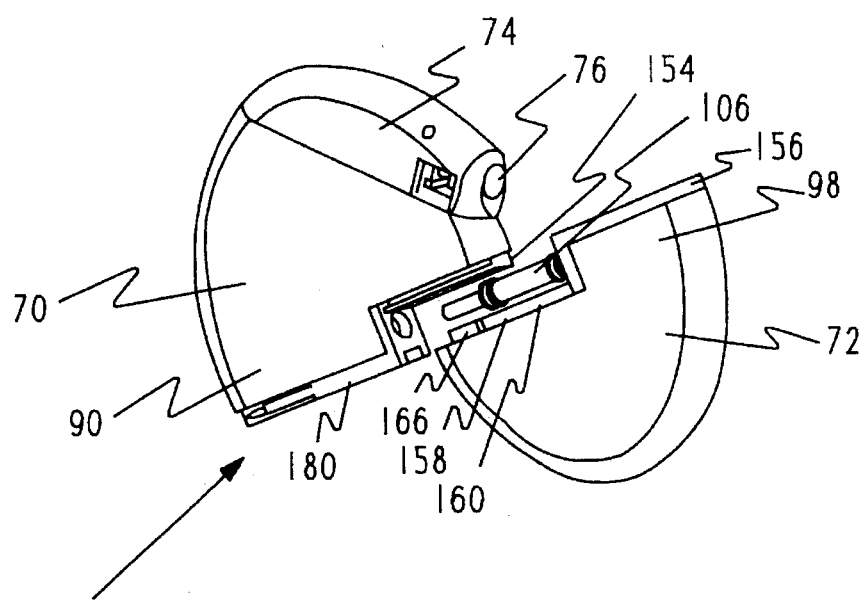
FIG. 5 is a perspective view of a disassembled pacemaker/defibrillator according to a second embodiment of our invention.
Figure 7:
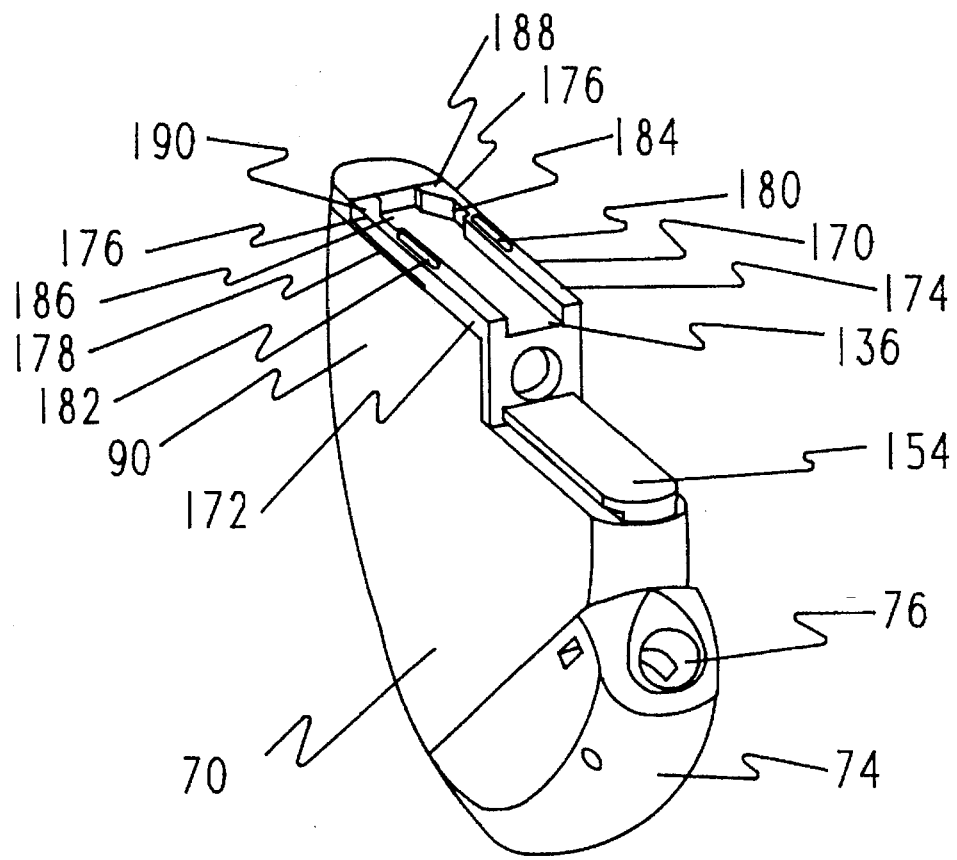
FIG. 7 is a perspective view of an electronic circuitry compartment of the embodiment of FIG. 5.
Figure 6:
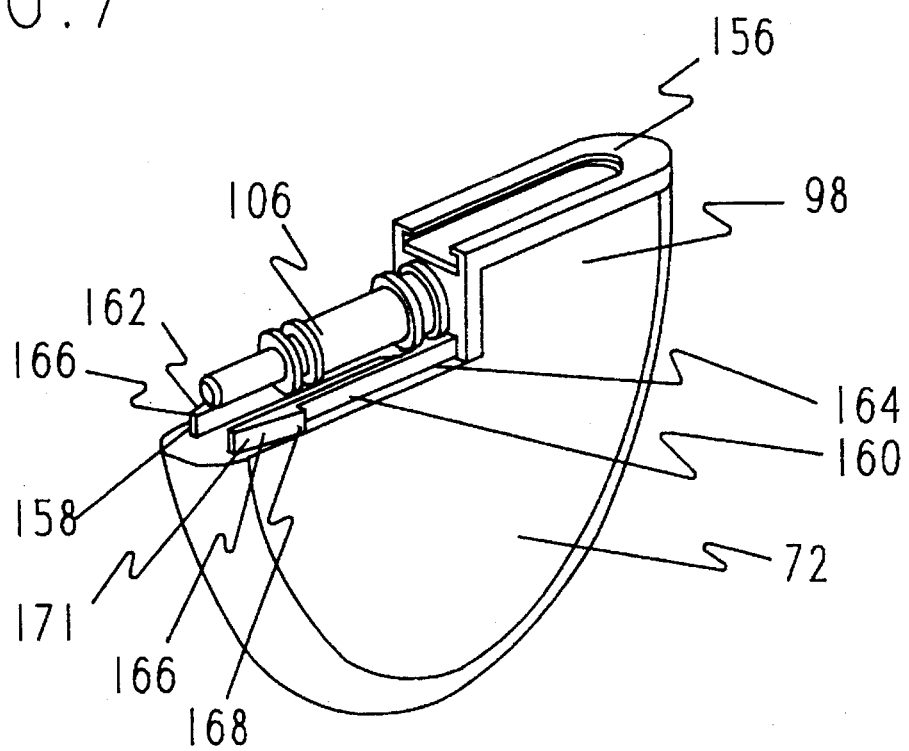
FIG. 6 is a perspective view of a battery compartment of the embodiment of FIG. 5.

FIGS. 5, 6, and 7 illustrate a second preferred embodiment of our invention. In the embodiment of FIGS. 5 through 7, a T-tongue 154 is substituted for one of the dovetail tongues and a T-groove 156 is substituted for one of the dovetail grooves of the embodiment of FIG. 4. The other dovetail groove and tongue are replaced by a slot and latch means. The slot and latch means comprise a bayonet pin 158, best seen in FIG. 6, and a mating slot, best seen in FIG. 7. The bayonet pin 158 comprises a pair of parallel arms 160, 162 having a proximal end 164 and a distal end 166. The arms 160, 162 are affixed at their distal ends 164 and are free to bend toward each other at their proximal end 166. Near the proximal ends 166 are outwardly directed prawls 168 and outwardly directed inclined surfaces 171.

The mating slot comprises a pair of parallel rails 170, 172. Each rail 170, 172 has a distal end 174 and a proximal end 176. Adjacent the distal end 174, the rail is substantially inflexible and may in fact be connected to the planar surface 136. Adjacent the proximal end 176, on the other hand, the rail 170 is relatively flexible and is not connected to the surface 176. A slot 178 extends between the proximal end 176 of the rail 170, 172 and the surface 136. Relief holes 180, 182 may be provided near the end of the slot 178 to increase the flexibility of the proximal ends of the arms. Indentations 184, 186 in the rails serve to selectively engage the prawls 168 on the arms 160, 162. Immediately adjacent the proximal ends of the rails 170, 172 are inwardly directed tabs 188, 190. In this embodiment, the two containers are connected together by sliding the T-tongue 154 into the T-groove 156 and by sliding bayonet pin between the rails 170, 172 until the prawls engage the indentations. To disassemble the device, compressive force may be applied to the proximal ends 176 of the rails 170, 172 perpendicular to those rails. This will compress the flexible proximal sections of the rails, pushing the tabs 188, 190 against the distal ends of their arms. Because the arms are free to bend over a longer distance than the proximal flexible sections of the rails, the prawls will be forced out of the indentations and it will be possible to withdraw the bayonet pin, disassembling the device. No additional tool is necessary.

Figure 8:
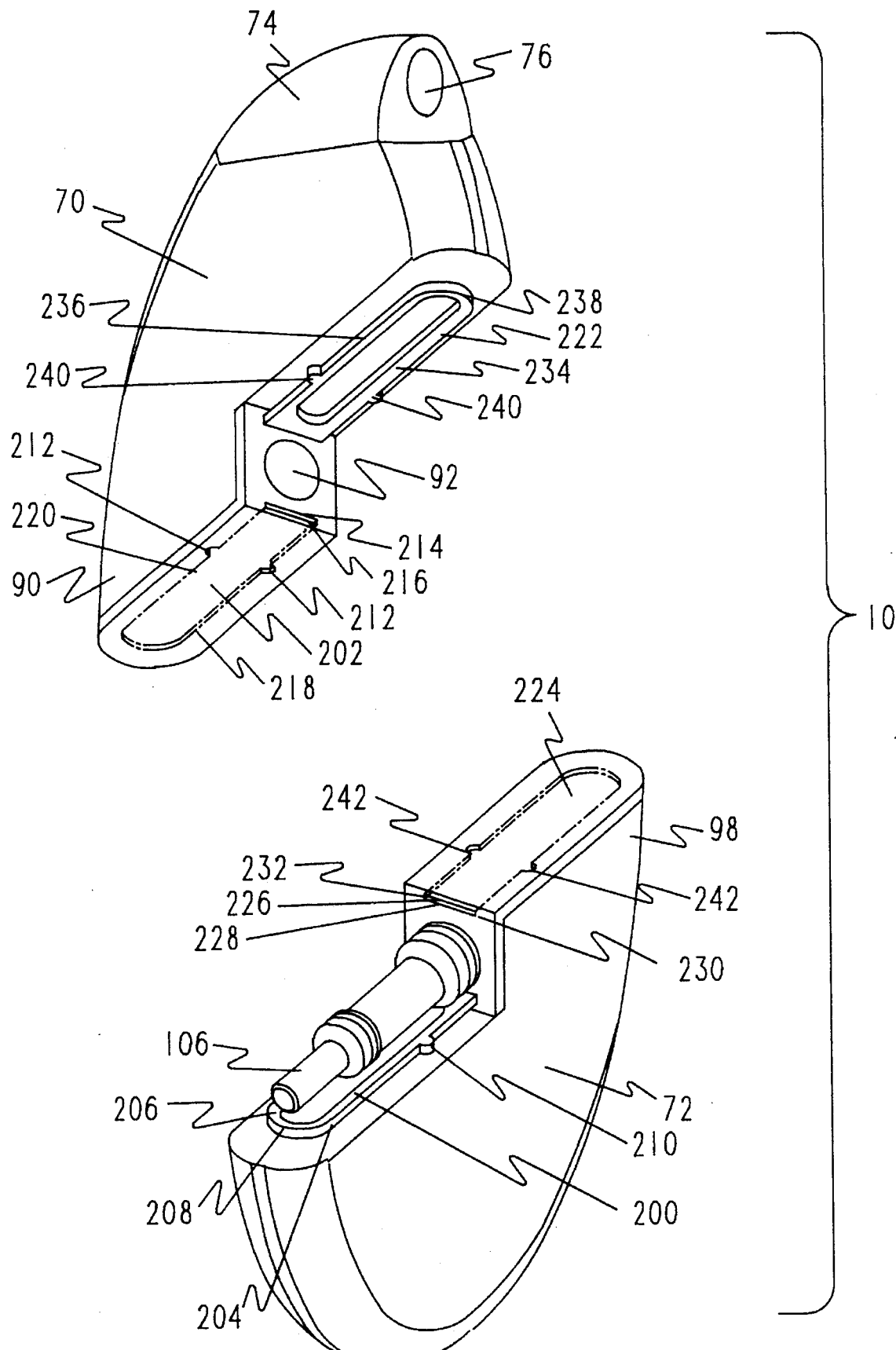
FIG. 8 is a perspective view of a disassembled pacemaker/defibrillator according to a third embodiment of our invention.

FIG. 8 illustrates a third, presently preferred, embodiment of our invention. In this embodiment, the electronics container 70 and the battery container 72 are connected by track means comprising sheaths and blades. On the battery container 72, for example, there is a first blade 200. The blade 200 lies substantially parallel to the pin 106, and is adapted to fit slidingly into a sheath 202, shown in phantom line, in the header like structure 90 of the electronics container 70. The sheath completely encloses the blade and has a top wall 214 and a parallel bottom wall 216 spaced apart therefrom. Side walls 218,220 connect the top and bottom walls. The blade 200 has two parallel arms 204, 206 connected at proximal end of the arms by a cross piece 208. The arms are slightly flexible or bendable. On each arm there is a tab 210. The tabs engage notches 212 in the side walls of the sheath 202 when the blade 200 is inserted into the sheath 202. Because the arms are bendable, the tabs spring out into the notches and resist disassembly. The two containers can be disassembled, however, without the use of a tool.

Additional stability can be provided by a second blade 222 on the electronics container 70 and a mating second sheath 224, shown in phantom line, in the header-like structure 98 of the battery container 72. The second sheath also has a top wall 226 and a parallel bottom wall 228 spaced apart therefrom. Side walls 230,232 connect the top and bottom walls. The blade 222 has two parallel arms 234,236 connected at proximal end of the arms by a cross piece 238. The arms are slightly flexible or bendable. On each arm there is a tab 240. The tabs engage notches 242 in the side walls of the sheath 224 when the blade 222 is inserted into the sheath 224.

Our invention may be embodied in other forms without departing from the teachings thereof. The foregoing description is intended, therefore to be illustrative, and not restrictive. The scope of our invention is defined by the following claims, and all equivalents are intended to be included therein.

We claim as our invention:

1. An implantable medical device comprising an electronic circuit;

a first container enclosing said electronic circuit said first container having a bottom side with at least a first substantially planar section and a second substantially planar section, said first and second planar sections of said bottom surface being offset from each other and being substantially parallel to each other;

a battery;

a second container enclosing said battery said second container having a top side with at least a first substantially planar section and a second substantially planar section, said first and second planar sections of said top surface being offset from each other and being substantially parallel to each other;

means for detachably coupling said electronic circuit and said battery; and means for mechanically coupling said first container to said second container, said means for mechanically coupling having interengagable track means along said substantially planar sections for connecting said containers by sliding said planar sections along each other from a disengaged position to an engaged position, said track means comprising a dovetail tongue on one of said substantially planar sections and a dovetail groove on another of said substantially planar sections.

2. The medical device according to claim 1 wherein said electronic circuit comprises a cardiac pacemaker circuit.

3. The medical device according to claim 1 wherein said electronic circuit comprises a defibrillator circuit.

4. An Implantable medical device comprising an electronic circuit;

a first container enclosing said electronic circuit said first container having a bottom side with at least one substantially planar section;

a battery;

a second container enclosing said battery means, said second container having a top side with at least one substantially planar section;

means for detachably coupling said electronic circuit and said battery; and means for mechanically coupling said first container to said second container, said means for mechanically coupling having interengagable track means along said substantially planar sections for connecting said containers by sliding said planar sections along each other from a disengaged position to an engaged position, said track means comprising a bayonet pin and a slot having a pair of opposed rails.

5. The medical device according to claim 4 wherein said bayonet pin comprises a pair of parallel arms, each arm engaging a rail, each rail having a proximal and a distal end and an indentation adjacent said proximal end, and each arm having a prawl on a distal end thereof, said prawl being adapted to engage the indentation in the rail engaging the arm.

6. The medical device according to claim 5 wherein said rails further comprise means for selectively disengaging said prawls from said indentations.

7. The medical device according to claim 6 wherein said means for selectively disengaging comprises a relatively inflexible section of said rail adjacent said distal end of said rail, a flexible section of said rail adjacent said proximal end of said rail, and a tab at said proximal end of said rail proximal from said flexible section, said tab being adapted to press against said distal end of said arm engaged in said rail whenever compressive force perpendicular to said rail is applied at said flexible section of said rail.

8. An implantable medical device comprising an electronic circuit;

a first container enclosing said electronic circuit said first container having a bottom side with at least one substantially planar section;

a battery;

a second container enclosing said battery said second container having a top side with at least one substantially planar section;

means for detachably coupling said electronic circuit and said battery; and means for mechanically coupling said first container to said second container, said means for mechanically coupling having interengagable track means along said substantially planar sections for connecting said containers by sliding said planar sections along each other from a disengaged position to an engaged position, said track means comprising a slot and latch means for engaging said slot, said slot comprising at least one rail having a proximal end, a distal end, a relatively inflexible section adjacent said distal end, a flexible section adjacent said proximal end, said flexible section forming an indentation, and a tab at said proximal end of said rail proximal from said flexible section and wherein said latch means comprise at least one arm engaging said rail, said arm having a prawl on a distal end thereof, said prawl being adapted to engage said indentation in said rail, said tab being adapted to press against said distal end of said arm whenever compressive force perpendicular to said rail is applied at said flexible section of said rail.

9. An implantable medical device comprising an electronic circuit;

a first container enclosing said electronic circuit said first container having a bottom side with at least one substantially planar section;

a battery;

a second container enclosing said battery, said second container having a top side with at least one substantially planar section;

for detachably coupling said electronic circuit and said battery; and means for mechanically coupling said first container to said second container, said means for mechanically coupling having interengagable track means along said substantially planar sections for connecting said containers by sliding said planar sections along each other from a disengaged position to an engaged position, said track means comprising a sheath on at least one of said containers, said sheath having a top wall and a parallel bottom wall spaced apart therefrom and at least one blade on the other of said containers, said blade being adapted to be slidingly received within said sheath.

10. The medical device according to claim 9 further comprising latch means for inhibiting withdrawal of said blade from said sheath.

11. The medical device according to claim 10 wherein said latch means comprise at least one tab on said blade and at least one notch in said sheath, said notch being placed to receive said tab when said blade is inserted within said sheath.

12. The medical device according to claim 11 wherein said blade has two parallel bendable arms and a cross piece joining said arms.

13. The medical device according to claim 12 wherein said electronic circuit comprises a cardiac pacemaker circuit.

14. The medical device according to claim 12 wherein said electronic circuit comprises a defibrillator circuit.

* * * * *